United States Patent [19]

Iwasaki et al.

[11] Patent Number: 4,562,736
[45] Date of Patent: Jan. 7, 1986

[54] METHOD OF DEFECT EVALUATION FOR CERAMIC PRODUCTS

[75] Inventors: Hideo Iwasaki, Sagamihara; Mamoru Izumi, Tokyo, both of Japan

[73] Assignee: Tokyo Shibaura Denki Kabushiki Kaisha, Kawasaki, Japan

[21] Appl. No.: 591,498

[22] Filed: Mar. 20, 1984

[30] Foreign Application Priority Data

Mar. 25, 1983 [JP] Japan .................................. 58-48748

[51] Int. Cl.$^4$ ............................................ G01N 29/04
[52] U.S. Cl. ..................................................... 73/587
[58] Field of Search ........................ 73/587, 801, 643; 374/57

[56] References Cited

U.S. PATENT DOCUMENTS

| | | | |
|---|---|---|---|
| 4,169,662 | 10/1979 | Kaule et al. | 73/643 |
| 4,255,971 | 3/1981 | Rosencwaig | 73/643 |
| 4,379,409 | 4/1983 | Primbsch et al. | 73/643 |
| 4,430,847 | 2/1984 | Quate | 73/643 |

OTHER PUBLICATIONS

Materials Evaluation (Dec. 1970), D. M. Romrell and L. R. Bunnell, "Monitoring of Crack Growth in Ceramic by Acoustic Emission," pp. 267-270.
Journal of American Ceramic Society, vol. 63 (1980), G. S. Kino et al., "Acoustic Surface Wave Measurements of Surface Cracks in Ceramics," pp. 65-71.
Ogneupory, No. 3 (1982), I. I. Nemets et al., "The Possibility of the Use of Acoustic Emission for Investigating the Heat Resistance of Refractories," pp. 144-147.

*Primary Examiner*—Anthony V. Ciarlante
*Attorney, Agent, or Firm*—Oblon, Fisher, Spivak, McClelland & Maier

[57] ABSTRACT

A ceramic product is exposed to a light from a tungsten lamp, so that a specified region of the product is heated. In this heating process, acoustic emissions from the ceramic product are detected by an AE sensor which is acoustically coupled to the ceramic product by means of a waveguide passage. A temperature gradient directed from the surface toward the inner part of the ceramic product is formed by heating, and thermal stress is applied to the product so that tensile stress is produced in the inner part of the product. In practical use, a crack constituting the core of fracture is caused to grow by the thermal stress, and an acoustic emission is released. The existence of a defect can be evaluated by detecting the acoustic emission. Also, the location of the defect in the product can be detected by heating part of the product. The equivalent crack dimension $a_e$ of the defect is obtained by measuring the rate of production of acoustic emission $dN/dt$, and the product can be checked for acceptability on the basis of the dimension $a_e$.

7 Claims, 10 Drawing Figures

F I G. 1
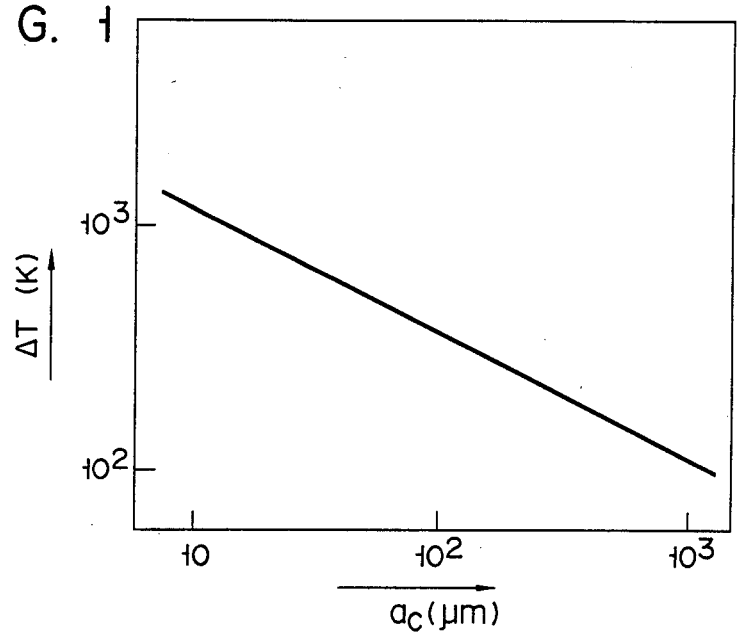
F I G. 2
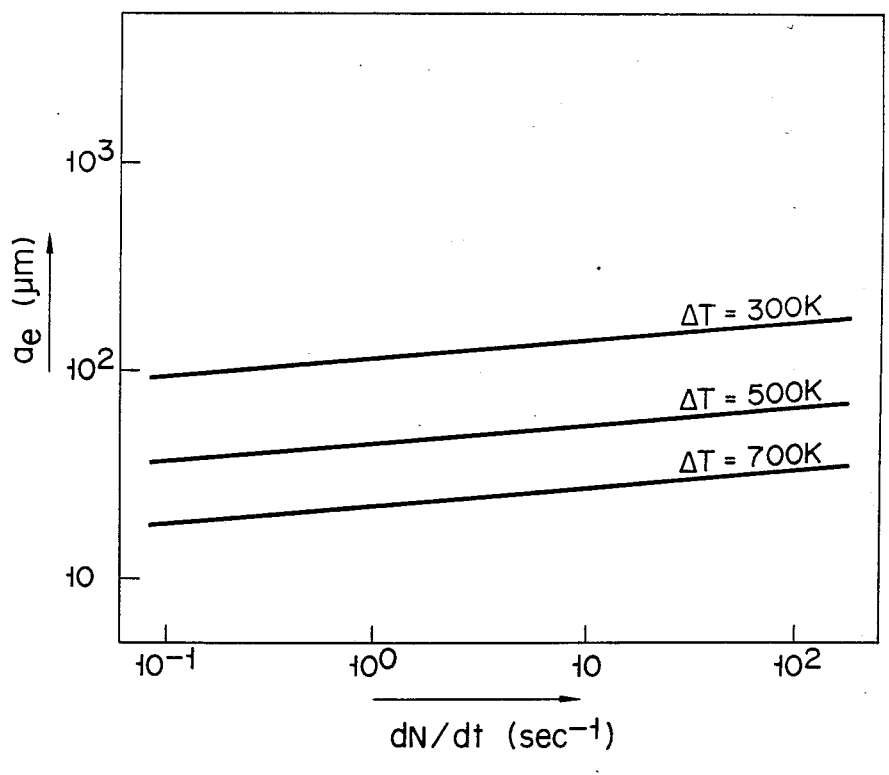

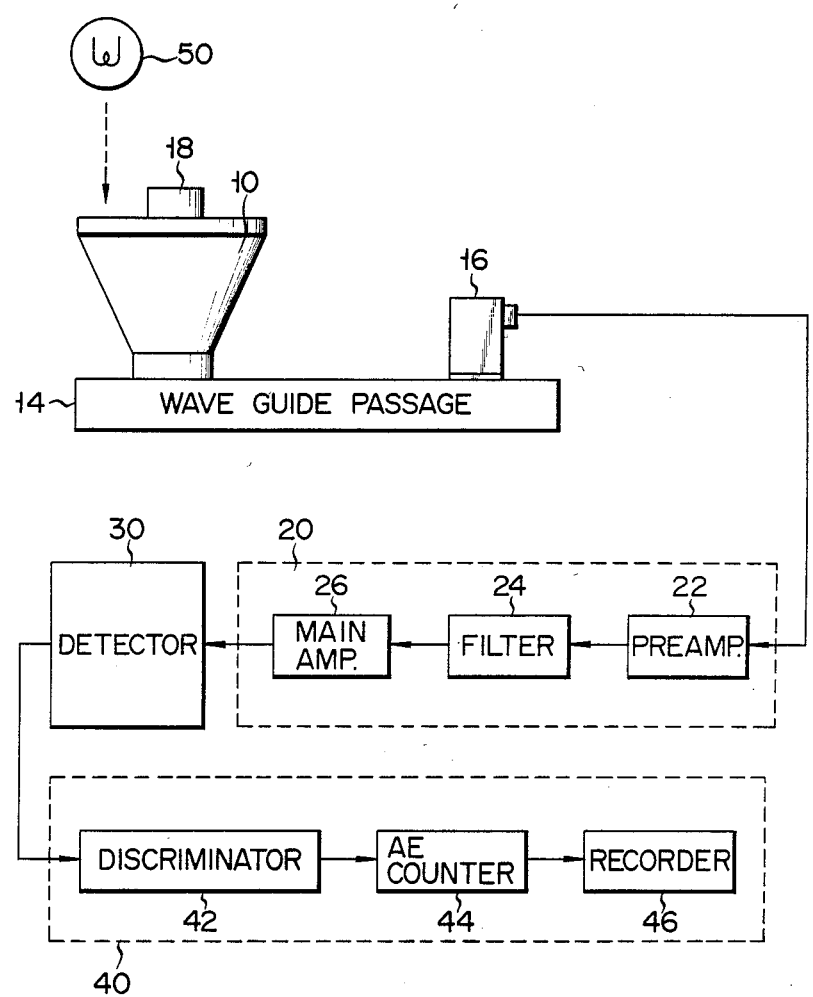

FIG. 7
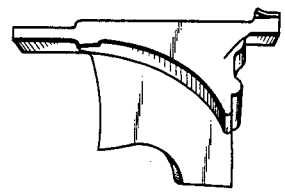
(a)
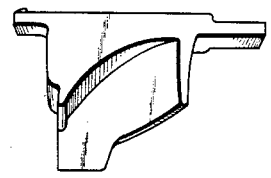
(b)
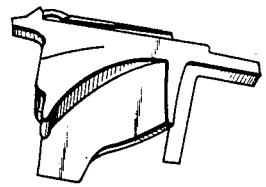
(c)

METHOD OF DEFECT EVALUATION FOR CERAMIC PRODUCTS

BACKGROUND OF THE INVENTION

1. Field of the Invention

The present invention relates to a method of defect evaluation or inspection capable of checking ceramic products of complicated shapes for defects.

2. Discussion of the Background

Ceramic products have the advantages in that they are strong and corrosion resistant under high-temperature condition, and are lightweight. With the recent development of ceramics with improved properties, research has been conducted to replace products made of conventional metal materials with ceramic products. Ceramics have a drawback, however, in that they are brittle and liable to fracture. Therefore, in using ceramic products in place of metallic ones, problems lie in their strength under actual temperature and stress conditions. In ceramic products, the occurrence of fracturing depends on the existence of the defects (especially defects near the surface portions), because fractures occur at the cracks or other defects. Accordingly, there is a demand for the development of a method for nondestructively detecting defects in ceramic products.

Nondestructive evaluating methods for metal products includes an ultrasonic pulse method (hereinafter referred to as UT method) and an acoustic emission method (hereinafter referred to as AE method). However, it is difficult to apply these methods directly to ceramic products. The size of cracks to be detected may be given in millimeters for metallic products, but is 0.1 mm or less for ceramic products. According to the prior art method, therefore, it is impossible to detect defects in ceramic products with high accuracy. Some of the cermaic products to be evaluated may have complicated shapes such as those of turbocharger rotors, not to mention plate-like, cylindrical or other simple configurations. Intricate shapes will result in various awkward situations, so that the incidence of ultrasonic waves and the detection of the reflected waves are difficult. Echoes will also reflect in a diffused manner to produce complex echoes, thereby concealing the existence of echoes of minor defects. Thus, it is hard to check ceramic products having intricate shapes for defects by the UT method.

Moreover, it is difficult to apply mechanical stress to ceramic products of complicated shapes. Therefore, it is also hard to make defect evaluation by the AE method in which mechanical stress is applied to produce acoustic emission.

SUMMARY OF THE INVENTION

The object of the present invention is to provide a method of defect evaluation for ceramic products capable of accurately detecting defects and the location thereof in ceramic products of complicated shapes.

According to the present invention, there is provided a method of defect evaluation for a ceramic product, which comprises the steps of heating the ceramic product to form a temperature gradient directed from the surface toward the inner part of the product, applying thermal stress so that tensile stress is produced in the inner part, and detecting acoustic emissions from the ceramic product produced by the thermal stress.

According to the method of the invention, tensile stress is produced inside the ceramic product by thermal stress without the use of any mechanical stress. Even though the ceramic product is complicated in shape, an acoustic emission can be produced from a defect existing in a specified region by applying tensile force to the specified region. Thus, defects of ceramic products with complicated configurations can be accurately detected.

Since ceramics are low in thermal conductivity, only a specific region of the product can be heated such that nondestructive evaluation may be conducted for the partial region only. Accordingly, it is possible to examine those portions of ceramic products which are subjected to high stress in practical use, or to partially check large ceramic products for defects. Also, the location of a defect in a ceramic product can be detected by dividing the surface of the ceramic product and heating each of the various regions, thereby applying thermal stress to each region and detecting acoustic emissions from the heated regions. In practical use, therefore, product weak spots can be identified. Furthermore, ceramic products may be checked for acceptability on the basis of an equivalent crack dimension $a_e$, which can be obtained according to the method of the invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 is a graph showing the relationship between the temperature difference $\Delta T$ and the critical crack dimension $a_c$;

FIG. 2 is a graph showing the relationship between the rate of production of acoustic emission $dN/dt$ and the equivalent crack dimension $a_e$;

FIG. 5 is a block diagram showing a second embodiment of the invention;

FIGS. 7(a), 7(b) and 7(c) are perspective views of sectioned samples; and

DESCRIPTION OF THE PREFERRED EMBODIMENTS

Figure 3:
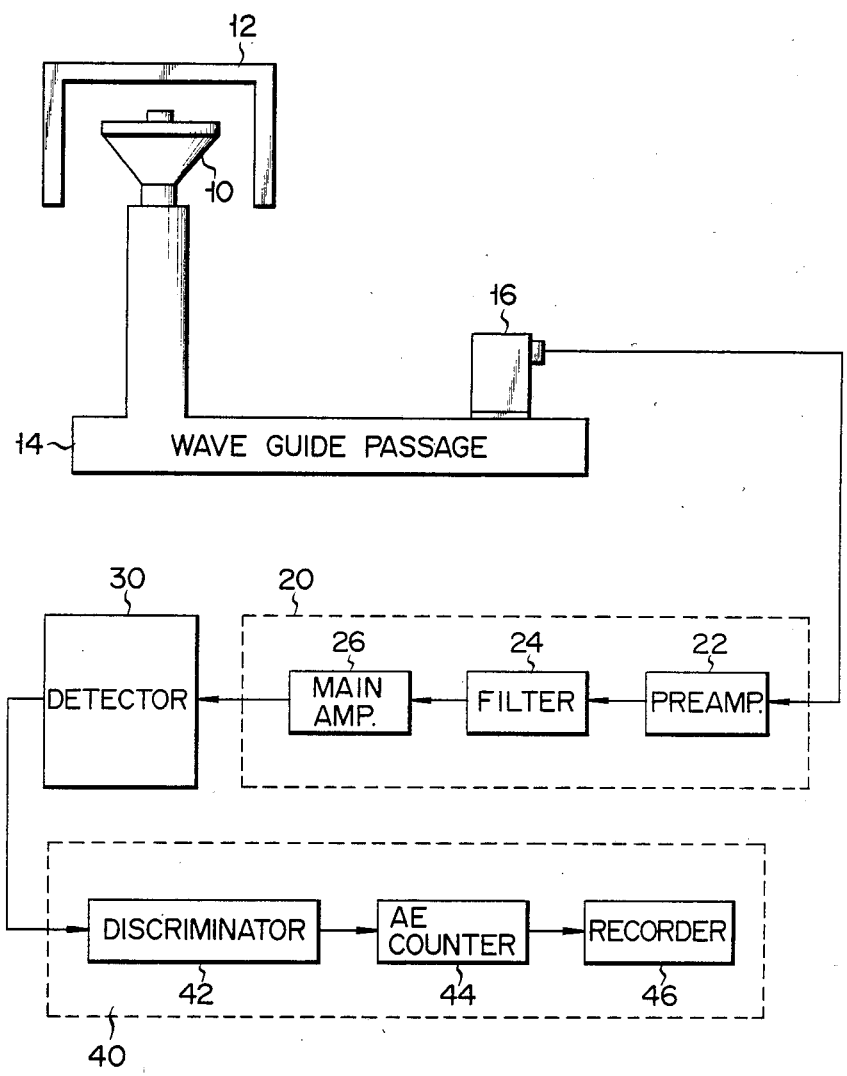
FIG. 3 is a block diagram showing a first embodiment of the present invention.

The present invention will now be described in detail. According to the method of the invention, a ceramic product is heated to produce a temperature gradient directed from the surface to the inner part of the product. The temperature gradient produces thermal stress in the ceramic product in a manner such that compressive stress exists in the surface portion and tensile stress in the inner part. If any defect (crack) exists in the inner part of the ceramic product, the tensile stress causes the crack to expand. As the crack expands, distortion energy is released to produce elastic waves. The existence of the defect may be detected by detecting acoustic emissions from the elastic waves.

The heating means used may be any means which can produce a temperature gradient directed from the surface to the inner part of a ceramic product, such as a tungsten lamp, laser beam, electric furnace, etc. A light from the lamp converged by means of an optical lens system, or a laser beam is locally applied to the ceramic product for local thermal stressing. A plurality of defects may be detected by suitably operating the heat source or by moving the ceramic product. As in the conventional method, acoustic emissions may be detected by an AE sensor which is attached to the ceramic product directly or by means of a waveguide passage.

Thermal stress may also be applied to the ceramic product by cooling the product. When cooling the product from room temperature, however, the temperature gradient obtained may be 290° K. at the most. Such a level of temperature gradient cannot provide highly accurate defect detection. If cooled to a very low temperature, the ceramic product will possibly change its properties. Since the thermal stress, produced in the inner part of the ceramic product by cooling, is compressive stress, cracks expand less than in the case where the inner part of the product is subjected to tensile stress, so that the sensitivity in defect detection is low. Accordingly, it is not advisable to apply thermal stress by cooling.

A method is proposed in which the thermal resistance of a ceramic product is measured by detecting acoustic emissions (I. I. Nemets et al.; Ogneupory, No. 3, pp. 144 to 147). According to this method, a ceramic product is first heated to about 1,000° C., and then an acoustic emission is detected as the product slowly cools. However, a crack which constitutes the core of the fracture expands while the ceramic product is being heated, so that the acoustic emission cannot be obtained from the crack even though thermal stress is applied at the time of cooling. Thus, defects cannot be detected by this method.

According to the present invention, thermal stress is applied to ceramic products by heating for the reasons described above. The heating speed should preferably be fast, since if heating is performed at a higher speed, greater thermal stress will be applied with a greater proportional impact, accelerating the production of the acoustic emissions.

Since the thermal conductivity of ceramics is lower than that of metals, the temperature gradient can be formed only in the vicinity of those regions to which a laser beam or the like is applied. Therefore, if a laser beam or a light converged by an optical lens system is locally applied, thermal stress is produced only in the region near the irradiated region. Accordingly, the acoustic emission detected by heating is generated from a partially heated region.

Thus, it is possible to examine only those portions of ceramic products which are subjected to high stress in practical use, or to partially check large ceramic products for detects, by taking advantage of the possibility of local thermal stressing. Also, the location of a defect in a ceramic product can be detected by applying thermal stress to each partial region of the product and detecting acoustic emission for each region. In practical use, therefore, weak spots of the products can be identified or information on the location of defects can be fed back to the manufacturing processes.

The equivalent crack dimensions of cracks may be calculated in the following manner after measuring the actual number of acoustic emissions produced and the number of acoustic emissions produced per unit time. The thermal stress $\sigma_T$ may be expressed as follows:

$$\sigma_T = KE\Delta T/(1-\nu), \quad (1)$$

where K is the coefficient of thermal expansion, E is the Young's modulus, $\nu$ is the Poissons ratio, and $\Delta T$ is the temperature difference.

If a crack is simulated by the use of a Griffith's model, the fracture stress $\sigma_f$ is expressed as follows:

$$\sigma_f = K_{1C}/Y\sqrt{a_c}, \quad (2)$$

where $2a_c$ is the critical crack dimension, $K_{1C}$ is the fracture toughness, and Y is the shape factor. A crack having a length larger than the critical crack length $2a_c$ may be caused to grow.

Since the thermal stress $\sigma_T$ required for the defect detection is given by $\sigma_T \geq \sigma_f$, the temperature difference $\Delta T$ to provide such thermal stress is given by $$\Delta T\sqrt{a_c} \geq K_{1C}(1-\nu)/YKE. \quad (3)$$

In the case of an engineering ceramics, e.g., $Si_3N_4$, its physical properties are as follows:

$K_{1C} = 5(MNm^{-3/2})$, $E = 310(GNm^{-2})$, $\nu = 0.25$, $K = 3.2 \times 10^{-6}(K^{-1})$ $Y = 1$, so that $\Delta T\sqrt{a_c}$ is given by $$\Delta T\sqrt{a_c} \geq 3.78. \quad (4)$$

FIG. 1 shows the relationship between the temperature difference $\Delta T$ and the critical crack dimension $a_c$. In FIG. 1, the axis of the abscissa represents the dimension $a_c$, and the axis of ordinate the difference $\Delta T$. If a temperature difference between 500° K. and 800° K. is provided, a crack of 20 to 50 microns can be caused to grow, as seen from FIG. 1. Therefore, the existence of a crack of 20 to 50 microns can be detected by heating the ceramic product for the temperature difference $\Delta T$ within the range from 500° K. to 800° K.

According to the present invention, the equivalent crack dimension may be obtained by detecting acoustic emission. In the case of $Si_3N_4$ and other ceramics, acoustic emissions depending on the speed of crack growth are produced with the growth of cracks (H. Iwasaki, M. Izumi and K. Ohta, "Acoustic emission during the process of crack growth in $Si_3N_4$ and $Al_2O_3$", Proc. of the 6th International Acoustic Emission Symposium, Susono, Japan, 1982). The rate of production of acoustic emission dN/dt and the speed of crack growth $V_c$ have the relationship as follows:

$$dN/dt = \beta V_c. \quad (5)$$

Here $\beta$ is given by $$\beta = dN/ds \cdot ds/da, \quad (6)$$

where dN/ds is the rate of production of acoustic emission against the increase of fracture per unit area, and ds/da is the rate of increase of fracture area against the increase of the crack length a. The crack growth speed $V_c$ is known by experience as follows:

$$V_c = a(K_1/K_0)^n. \tag{7}$$

Here n is a natural number, $K_0(=1MNm^{-3/2})$ is a normalization factor, and $K_1$ is a stress intensity factor given by $$K_1 = Y\sigma\sqrt{a}, \tag{8}$$

where $\sigma$ is applied stress. The values $\alpha$, $\beta$ and n can be experimentally obtained by measuring acoustic emission by the double torsion method. These values are constants, which are determined by the kind of material, if the acoustic emission measuring conditions are constant. The relationship between the rate of production of acoustic emission dN/dt and the crack length a can be obtained from eqs. (6), (7) and (8). The equivalent crack dimension $a_e$ of a ceramic product can be calculated as follows:

$$\log_{10} a_e = \{2/(2+n)\}\{\log_{10}(dN/dt) + \log_{10}(G(\Delta T))\}, \tag{9}$$

where $G(\Delta T) = (\frac{1}{2}\pi\alpha)(dN/ds)^{-1} \cdot \{KE/(1-\nu)K_0\}^{-n}\Delta T^{-n}$. In the case of $Si_3N_4$, $\alpha = 1.4 \times 10^{-18}$ (m/s), $N=21$, and $dN/ds = 8.2 \times 10^7$ (m$^{-2}$), so that the rate of production of acoustic emission dN/dt and the equivalent crack dimension $a_e$ have the relationships shown in FIG. 2 where $\Delta T = 300°$, 500° and 700° K., if the stress applied to the ceramic product in practical use is given, the ceramic product can be checked for acceptability in accordance with the equivalent crack dimension $a_e$ obtained in this manner. According to this method of decision, if the equivalent dimension of a crack constituting the core of fracture is $a_1$, those products, which produce no acoustic emission or produce acoustic emissions but under the condition $a_e < a_1$, are judged acceptable, and others are judged defective.

Preferred embodiments of the present invention will now be described with reference to the accompanying drawings. FIG. 3 shows a first embodiment of the invention. In this embodiment, a ceramic product 10, e.g., a turbocharger rotor formed of $Si_3N_4$, is heated whole. The ceramic product 10 is placed in a small electric furnace 12 as the heating means. One end of a wave-guide passage 14 made of $Si_3N_4$ is fixed to the product 10 by using silicone oil or the like. An AE sensor 16 is fixed to the other end of the wave-guide passage 14 by means of silicone oil or the like. The output of the AE sensor 16 is applied to the input of an amplifier unit 20. The amplifier unit 20 includes, for example, a preamplifier 22 of 40 db, a high-pass filter 24 of 50 kHz, and a main amplifier 26 of 50 db. A detection signal from the AE sensor 16, cleared of noise below 50 kHz and amplified by the amplifier unit 20, is applied to an AE signal processing unit 40 through a detector 30. The processing unit 40 includes a discriminator 42 with the threshold voltage of 0.5 V, a counter 44, and a recorder 46. The detection signal from the AE sensor is cleared of noise and converted into pulses by the discriminator 42. The pulses are counted by the counter 44, and recorded as a function of time by the recorder 46. The rate of production of acoustic emission dN/dt is calculated from the recorded count number. Table 1 shows the results of defect evaluation on three rotors (Samples 1 to 3) with the temperature difference $\Delta T$ or 500° K.

TABLE 1

| SAMPLE | 1 | 2 | 3 |
|---|---|---|---|
| Number of AE produced | 0 | 175 | 0 |
| Rate of production of AE dN/dt | — | 18 | — |
| Equivalent crack dimension $a_e$ | — | 58 | — |

Figure 4:
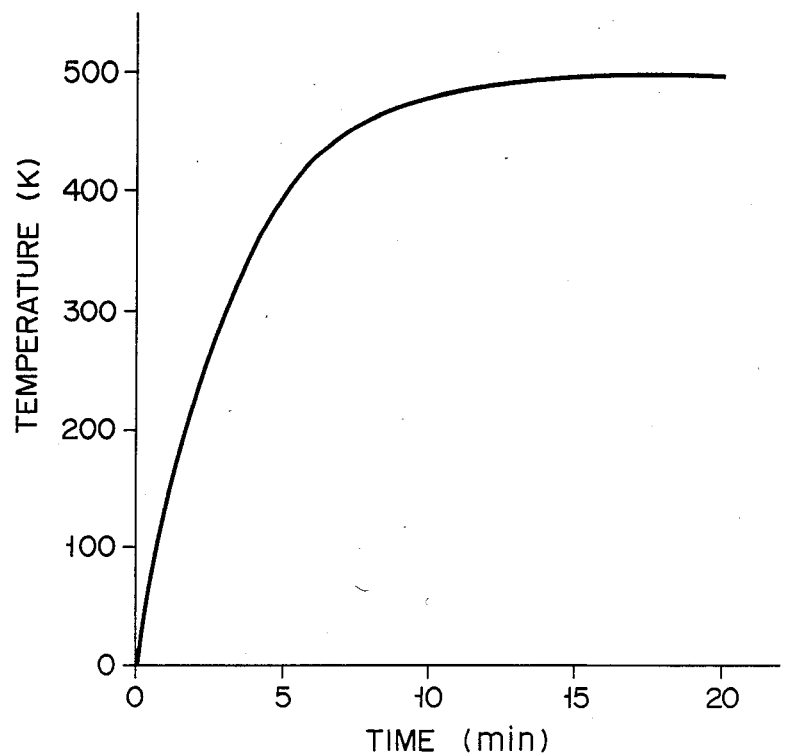
FIG. 4 is a graph showing the heating speed.

The surface heating speed of the product 10 is as shown in FIG. 4. The number of acoustic emissions produced is the total of acoustic emissions produced in three minutes after the start of heating, while the rate of production of acoustic emission is the time-based change of the number of acoustic emissions produced steadily. Table 1 also shows the equivalent crack dimension $a_e$ calculated from eq. (9). Since no acoustic emission is detected from Samples 1 and 3, it may be understood that Samples 1 and 3 are not subject to cracks or any other defects. On the other hand, Sample 2 may be presumed to be subject to a defect with an equivalent crack dimension of 58 microns.

Figure 6:
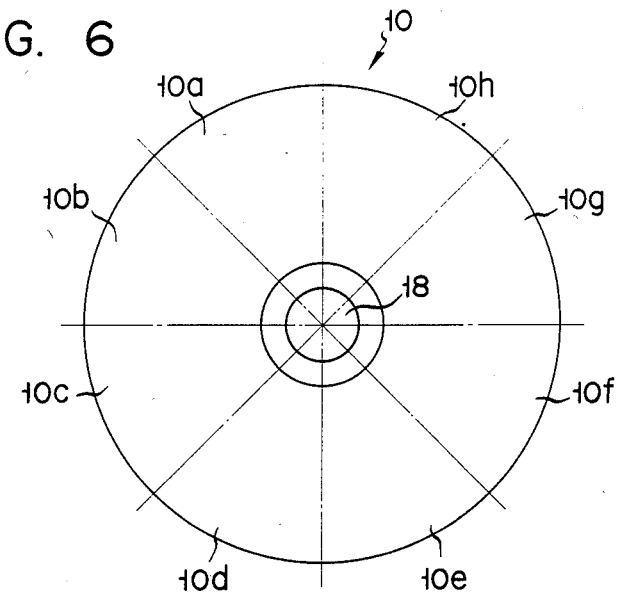
FIG. 6 is a plan view of a rotor.

Referring now to FIGS. 5 and 6, a second embodiment of the invention will be described. In FIG. 5, like reference numerals are used to designate like components used in the first embodiment shown in FIG. 3. Description of those components will be omitted. In this second embodiment, as shown in the plan view of FIG. 6, the bottom face of a blade of a turbocharger rotor (product 10) is divided into eight equal regions 10a, 10b, 10c, 10d, 10e, 10f, 10g and 10h, which are each checked for detect. In this embodiment, a tungsten lamp 50 is used for the heating means. The lamp 50 has, for example, 150-W output and 20-mm focal distance. The lamp 50 is set in a manner such that it can rotate about the rotation axis 18 of the product 10. A light from the lamp 50 is applied to each region for a 30 second scan. The temperature difference $\Delta T$ used is 600° K. Acoustic emissions produced from the product 10 are detected by the AE sensor 16, which is disposed on the waveguide passage 14 at a distance of about 10 cm from the product 10. Table 2 shows the results of defect evaluation on an additional five samples (Samples 4 to 8).

TABLE 2

| SAMPLE | Region applied thermal stress | | | | | | | |
|---|---|---|---|---|---|---|---|---|
| | 10a | 10b | 10c | 10d | 10e | 10f | 10g | 10h |
| 4 Number of AE produced | 0 | 0 | 0 | 0 | 0 | 0 | 0 | 0 |
| Rate of production of AE dN/dt | — | — | — | — | — | — | — | — |
| Equivalent crack dimension $a_e$ | — | — | — | — | — | — | — | — |
| 5 Number of AE produced | 0 | 0 | 0 | 64 | 0 | 0 | 0 | 0 |
| Rate of production of AE dN/dt | — | — | — | 30 | — | — | — | — |
| Equivalent crack dimension $a_e$ | — | — | — | 60 | — | — | — | — |
| 6 Number of AE produced | 0 | 0 | 0 | 0 | 0 | 0 | 0 | 0 |
| Rate of production of | — | — | — | — | — | — | — | — |

TABLE 2-continued

| SAMPLE | | Region applied thermal stress | | | | | | | |
|---|---|---|---|---|---|---|---|---|---|
| | | 10a | 10b | 10c | 10d | 10e | 10f | 10g | 10h |
| | AE dN/dt Equivalent crack dimension $a_e$ | — | — | — | — | — | — | — | — |
| 7 | Number of AE produced | 0 | 0 | 0 | 0 | 0 | 0 | 0 | 0 |
| | Rate of production of AE dN/dt | — | — | — | — | — | — | — | — |
| | Equivalent crack dimension $a_e$ | — | — | — | — | — | — | — | — |
| 8 | Number of AE produced | 276 | 120 | 10 | 0 | 1 | 0 | 0 | 0 |
| | Rate of production of AE dN/dt | 36 | 24 | 1.3 | — | — | — | — | — |
| | Equivalent crack dimension $a_e$ | 62 | 59 | 43 | — | — | — | — | — |

As seen from Table 2, Sample 5 has defects in its region 10d, while Sample 8 has defects in its regions 10a, 10b and 10c. In order to prove the accuracy of the defect evaluation by acoustic emission detection, Samples 4 to 8 were cut in the center of each region, and sections were observed by the naked eye and through an optical microscope for detection of cracks. As a result, cracks were found only in those regions in which acoustic emissions were produced. FIGS. 7(a), 7(b) and 7(c) show the sections of the region 10d of Sample 5, the region 10e of Sample 7, and the region 10a of Sample 8, respectively. Cracks are found in the samples of FIGS. 7(a) and 7(c), and no crack in the sample of FIG. 7(b). Thus, the existence of cracks is highly responsive to the production of acoustic emissions, indicating the high accuracy of the defect detection method according to the present invention. According to this embodiment, the location of cracks, as well as the existence thereof, can be detected.

Figure 8:
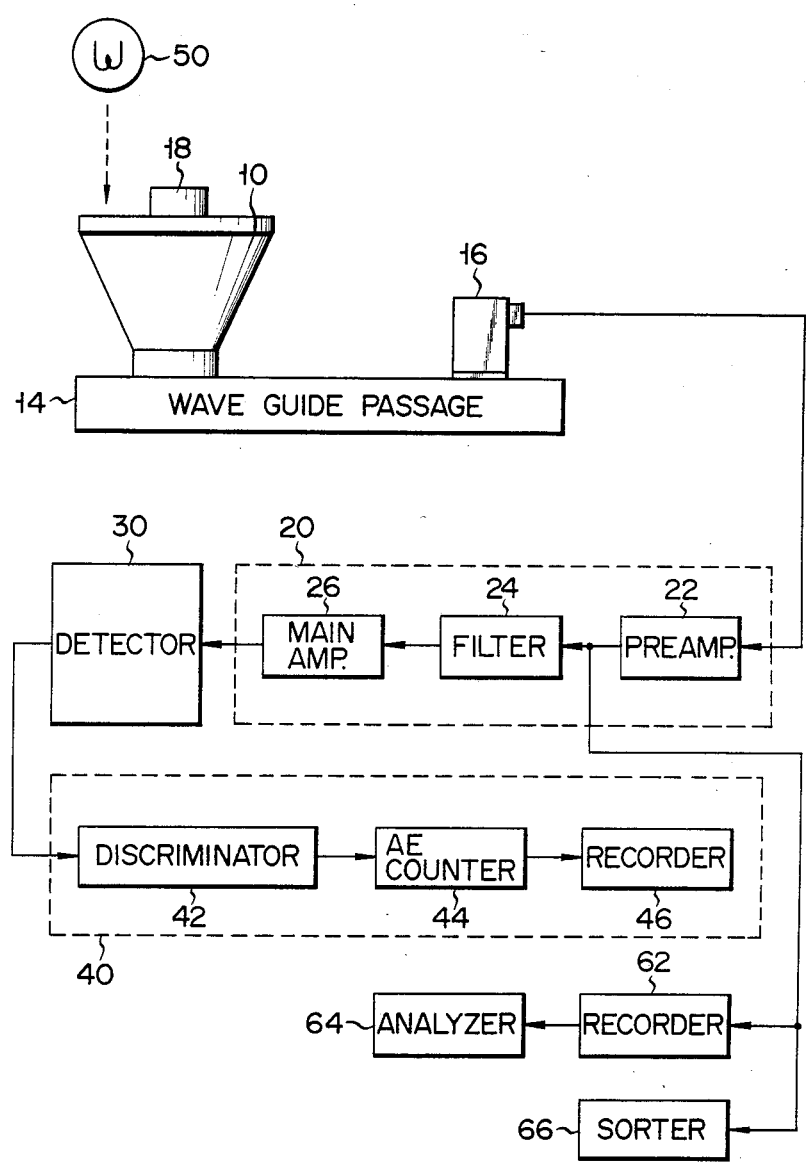
FIG. 8 is a block diagram showing a third embodiment of the invention.

Referring now to FIG. 8, a third embodiment of the invention will be described. In FIG. 8, like reference numerals are used to designate like components shown in FIG. 5. Description of those components will be omitted. The output of the preamplifier 22 is also applied to a waveform recorder 62 and an AE amplitude distribution sorter 66. The output of the waveform recorder 62 is applied to a frequency analyzer 64. In this embodiment, the waveform, frequency and amplitude distribution can be obtained by means of the waveform recorder 62, the frequency analyzer 64, and the AE amplitude distribution sorter 66.

Obviously, numerous modifications and variations of the present invention are possible in light of the above teachings. It is therefore to be understood that within the scope of the appended claims, the invention may be practiced otherwise than as specifically described herein.

What is claimed is:

1. A method of nondestructive defect evaluation for a ceramic product, which comprises:
heating the ceramic product to produce a temperature difference within a range from 500° K. to 800° K. and form a temperature gradient directed from a surface toward an inner part of the product so as to produce tensile stress in an inner part of said ceramic product by thermal stress; and
detecting acoustic emissions from the ceramic product from cracks 20 to 50 microns in size produced by the tensile stress during the heating of the ceramic product.

2. The method according to claim 1, wherein the surface of said ceramic product is divided into a plurality of regions so that a specific one of said regions is heated and subjected to the thermal stress.

3. The method according to claim 2, wherein said ceramic product is heated by a tungsten lamp or a laser beam.

4. The method according to claim 1, wherein the surface of said ceramic product is divided into a plurality of regions so that each said region is heated and subjected to the thermal stress, and acoustic emissions from each heated region are detected.

5. The method according to claim 1, further comprising steps of detecting the number of acoustic emissions produced per unit time (dN/dt) and calculating an equivalent crack dimension $a_e$ from said number of acoustic emissions (dN/dt).

6. The method according to claim 5, wherein said equivalent crack dimension $a_e$ is calculated as follows:

$$\log_{10} a_e = \{2/(2+n)\}\{\log_{10}(dN/dt) + \log_{10}(G(\Delta T))\},$$

where n is a natural number and a constant depending on the material of the ceramic product, and $G(\Delta T)$ is given by $$G(\Delta T) = (\tfrac{1}{2}\pi a)(dN/ds)^{-1}\{KE/(1-\nu)K_0\}^{-n}\Delta T^{-n},$$

where dN/ds is the rate of production of acoustic emission against the increase of fracture per unit area, K is the coefficient of thermal expansion, $\nu$ is the Poissons ratio, $\Delta T$ is the temperature difference, E is the Young's modulus, and $\alpha$ is a constant depending on the material of the ceramic product and given by $$\alpha = V_c/(K_1/K_0)^n,$$

where $V_c$ is the speed of crack growth, $K_1$ is the stress intensity factor, and $K_0$ is a normalization factor.

7. The method according to claim 1, wherein said the whole ceramic product is heated in an electric furnace.

* * * * *